United States Patent
Grove Sund et al.

(10) Patent No.: US 10,736,769 B2
(45) Date of Patent: Aug. 11, 2020

(54) TOUCH MAPPING

(71) Applicant: Coloplast A/S, Humlebaek (DK)

(72) Inventors: Anders Grove Sund, Dyssegaard (DK); Lasse Hylleberg Mølleskov, Copenhagen (DK); Esben Strøbech, Hoersholm (DK)

(73) Assignee: Coloplast A/S, Humlebaek (DK)

( * ) Notice: Subject to any disclaimer, the term of this patent is extended or adjusted under 35 U.S.C. 154(b) by 1065 days.

(21) Appl. No.: 14/905,812

(22) PCT Filed: Jul. 15, 2014

(86) PCT No.: PCT/DK2014/000038
§ 371 (c)(1),
(2) Date: Jan. 17, 2016

(87) PCT Pub. No.: WO2015/007284
PCT Pub. Date: Jan. 22, 2015

(65) Prior Publication Data
US 2016/0151196 A1  Jun. 2, 2016

(30) Foreign Application Priority Data

Jul. 18, 2013 (DK) ................................. 2013 70407
Jun. 12, 2014 (DK) ................................. 2014 70351

(51) Int. Cl.
*A61F 5/44* (2006.01)
*A61F 5/443* (2006.01)

(52) U.S. Cl.
CPC ............ *A61F 5/4404* (2013.01); *A61F 5/443* (2013.01)

(58) Field of Classification Search
CPC combination set(s) only.
See application file for complete search history.

(56) References Cited

U.S. PATENT DOCUMENTS

| | | | |
|---|---|---|---|
| 4,286,603 A | 9/1981 | Marshall | |
| 4,693,236 A | 9/1987 | Leprevost | |
| 4,699,146 A | 10/1987 | Sieverding | |
| 4,983,171 A | 1/1991 | Schirmer | |
| 5,714,225 A | 2/1998 | Hansen et al. | |
| 5,942,186 A * | 8/1999 | Sanada | A61F 5/443 252/964 |
| 6,171,289 B1 | 1/2001 | Millot et al. | |
| 6,239,190 B1 | 5/2001 | Wilkinson et al. | |
| 6,929,627 B2 | 8/2005 | Mahoney | |
| 7,105,715 B2 * | 9/2006 | Carlucci | A61F 13/42 604/359 |
| 7,260,999 B2 * | 8/2007 | Divigalpitiya | H01H 1/029 73/774 |
| 7,483,731 B2 * | 1/2009 | Hoarau | A61B 5/14552 600/310 |
| 7,506,543 B2 | 3/2009 | Chiodo et al. | |
| 7,727,547 B2 | 6/2010 | Fortune et al. | |
| 7,737,321 B2 * | 6/2010 | Elliott | A61F 5/445 200/61.04 |
| 7,770,473 B2 | 8/2010 | Lilienfeld-Toal et al. | |
| 7,807,007 B2 | 10/2010 | Tachauer et al. | |
| 8,133,336 B2 | 3/2012 | Kettlewell et al. | |
| 8,133,504 B2 | 3/2012 | Kettlewell et al. | |
| 8,152,748 B2 | 4/2012 | Randolph | |
| 8,319,003 B2 | 11/2012 | Olsen et al. | |
| 8,349,358 B1 | 1/2013 | McBride | |
| 8,398,603 B2 * | 3/2013 | Thirstrup | A61F 5/445 604/304 |
| 8,409,158 B2 | 4/2013 | Edvardsen et al. | |
| 8,530,720 B2 | 9/2013 | Freer et al. | |
| 8,545,469 B2 | 10/2013 | Andresen et al. | |
| 9,066,812 B2 * | 6/2015 | Edvardsen | A61F 5/4404 |
| 2002/0192829 A1 * | 12/2002 | Zainiev | A61F 13/02 436/39 |
| 2004/0049187 A1 | 3/2004 | Burnett et al. | |
| 2004/0078219 A1 * | 4/2004 | Kaylor | G06F 19/3418 705/2 |
| 2005/0260544 A1 | 11/2005 | Jones et al. | |
| 2007/0009582 A1 | 1/2007 | Madsen et al. | |
| 2008/0026015 A1 | 1/2008 | MacDonald et al. | |
| 2008/0275327 A1 * | 11/2008 | Faarbaek | A61B 5/04087 600/382 |
| 2009/0118686 A1 | 5/2009 | Playdon | |
| 2009/0204100 A1 * | 8/2009 | Van Pieterson | A61B 5/0008 604/503 |
| 2009/0234312 A1 * | 9/2009 | O'Toole | A61F 5/4405 604/332 |
| 2009/0240219 A1 | 9/2009 | Barcroft | |
| 2010/0030167 A1 * | 2/2010 | Thirstrup | A61F 5/445 604/318 |
| 2010/0121291 A1 | 5/2010 | Davies et al. | |
| 2011/0106032 A1 * | 5/2011 | Kratky | A61F 5/445 604/337 |
| 2011/0319787 A1 * | 12/2011 | Lamoise | A61B 5/103 600/549 |
| 2012/0130297 A1 | 5/2012 | Loescher | |
| 2012/0143154 A1 * | 6/2012 | Edvardsen | A61F 5/4404 604/318 |

(Continued)

FOREIGN PATENT DOCUMENTS

| CN | 201564674 U | 9/2010 |
|---|---|---|
| DE | 3836590 A1 | 5/1990 |
| DE | 202007017527 U1 | 3/2008 |

(Continued)

*Primary Examiner* — Tatyana Zalukaeva
*Assistant Examiner* — Guy K Townsend
(74) *Attorney, Agent, or Firm* — Coloplast Corp., Coloplast A/S; Nick Baumann

(57) ABSTRACT

A method of monitoring the pressure applied to an ostomy appliance during application to the skin, the ostomy appliance comprising an adhesive wafer comprising a backing layer facing away from the skin and an adhesive layer for attachment to the skin, the method comprising the steps of: providing sensing means capable of recording application of pressure to the wafer, applying the adhesive wafer to the skin surrounding the stoma by applying pressure to the sensing means and wafer and retrieving the recorded data from the sensing means.

21 Claims, No Drawings

(56) References Cited

U.S. PATENT DOCUMENTS

| | | |
|---|---|---|
| 2012/0143155 A1* | 6/2012 | Edvardsen ............ A61F 5/4404 604/318 |
| 2012/0165717 A1 | 6/2012 | Khaburi |
| 2012/0283678 A1 | 11/2012 | Nguyen-Demary et al. |
| 2013/0116636 A1 | 5/2013 | Carrubba |
| 2016/0151196 A1* | 6/2016 | Grove Sund ......... A61F 5/4404 604/318 |

FOREIGN PATENT DOCUMENTS

| | | | |
|---|---|---|---|
| GB | 1601735 | A | 11/1981 |
| GB | 2300808 | A1 | 11/1996 |
| GB | 2473227 | A1 | 3/2011 |
| JP | 2011026733 | A2 | 2/2011 |
| KR | 20120084284 | A | 7/2012 |
| WO | 9101118 | A1 | 2/1991 |
| WO | 9101119 | A1 | 2/1991 |
| WO | 9418919 | A1 | 9/1994 |
| WO | 0010618 | A1 | 3/2000 |
| WO | 0079497 | A1 | 12/2000 |
| WO | 0130405 | A1 | 5/2001 |
| WO | 06032924 | A1 | 3/2006 |
| WO | 09144615 | A1 | 12/2009 |
| WO | WO-2011003420 A1 * | | 1/2011 ............. A61F 5/443 |

\* cited by examiner

TOUCH MAPPING

The invention relates to a method of monitoring the pressure applied to an ostomy appliance during application to the skin. The invention further relates to ostomy appliances with means for monitoring the pressure applied to an ostomy appliance during application to the skin.

BACKGROUND

In connection with surgery for a number of diseases in the gastro-intestinal tract, one of the consequences in many cases is that the patient is left with an abdominal stoma, such as a colostomy, an ileostomy or a urostomy in the abdominal wall for the discharge of visceral contents. The discharge of visceral contents cannot be regulated at will. For that purpose, the user will have to rely on an appliance to collect the material emerging from such opening in a bag, which is later emptied and/or discarded at a suitable time.

An ostomy appliance may be in the form of a one-piece appliance for which a collecting bag for human body wastes is permanently, or fixedly, secured to an adhesive base plate for attachment to the human skin. Alternatively, the ostomy appliance may be a two-piece appliance comprising a base plate and a collecting bag which may be coupled to and un-coupled from each other through a coupling means. This has the effect that the base plate does not need to be separated from the skin of the user as often as exchange of the collecting bag requires. The base plate may need only to be changed every third or fourth day depending on the user, whereas the collecting bag may be changed more than once per day. Typically, it is desirable to need as few exchanges of the base plate as possible in order to reduce the risk of skin complications.

One of the main concerns of ostomates using ostomy appliances having an adhesive base plate for attachment to the skin surrounding a stoma, and where a collecting bag is attached to the base plate for collecting stoma output, is leakage or even complete detachment of the ostomy appliance.

Numerous attempts have been made to solve this problem and even though some attempts have been partly successful, still there exist no products that completely solve this problem.

One reason why this is so difficult to solve is the fact that stomas and peoples anatomy are very different. Different considerations need to be made for thin people than for larger people, for different skin types, for placement of the stoma which may vary a lot from person to person, for scar tissue surrounding the stoma, local irregular skin topography, e.g. a hernia, and more—and in particular combinations of all of the above.

Another reason may be the way the adhesive wafer is applied to the skin surrounding the stoma. If the wafer is not sufficiently fixed to the skin due to carelessness or inattentive application, leaks may occur. The adhesive used for ostomy appliances are typically pressure sensitive adhesives, meaning that application of pressure to the adhesive enhances the adhesive tack of the adhesive, thus it attaches better to the skin. In several cases, ostomy bag users do not apply pressure enough to the adhesive base plate of the bag sufficiently to maintain the adhesive capabilities as well as they may neglect to apply pressure over the entire wafer, due to carelessness or reduced dexterity of the user's hands. This may cause leakage from the stoma.

This problem has been tried solved by using a stronger adhesive, but this may give rise to other problems, as this is more aggressive to the skin and more difficult to remove from the skin. Furthermore, a stronger adhesive may still not be enough, it is equally important that the wafer is mounted sufficiently.

Thus, there is a need to further develop and find improvements in order to solve this problem. In other words, there exists a need to monitor that the ostomy wafer is correctly applied to the user.

SUMMARY OF THE INVENTION

One aspect of the invention is to record the user's pattern of movements during application of an ostomy wafer.

An aspect of the invention is to provide an education tool for (new) users of ostomy appliances.

An aspect is to provide feedback to the user, in order to inform them about where and whether or not they have applied sufficient pressure to the wafer.

DETAILED DESCRIPTION OF THE INVENTION

In a first aspect, the invention relates to a method of monitoring the pressure applied to an ostomy appliance during application to the skin, the ostomy appliance comprising an adhesive wafer comprising a backing layer facing away from the skin and an adhesive layer for attachment to the skin, the method comprising the steps of: providing sensing means capable of recording application of pressure to the wafer, applying the adhesive wafer to the skin surrounding the stoma by applying pressure to the sensing means and wafer and retrieving the recorded data from the sensing means.

The method may serve to help and inform the user during application of the wafer. By the method of the invention, the user is provided with direct feedback to the quality of application process and this may cause the user to be more alert when applying the wafer, knowing which areas of the wafer that are important to address and which areas that may need an extra impact.

The method reveals where the users touch and press the wafer during application to the skin surrounding the stoma. The retrieved data from the application process may disclose that the user fails to attach the entire adhesive surface correctly to the skin and thus teach him to attend these forgotten areas. The adhesive used for such ostomy wafers typically comprises two types of polymers; a tacky polymer and a viscous polymer, and if a user is not thorough enough in pressing the adhesive to the skin during application, it may only be the tacky polymer that is attaching to the body. The method of the invention renders it possible to map where, and how hard the user applies enough pressure—and where not.

The method of the invention renders it possible to measure, monitor and log, where the users touch the wafer when they are applying it. This may be useful information both for the user in the daily care and also for the health care people instructing new users.

The retrieved data from the application process may be used to reconstruct the course of actions. Reconstruction of the applied pressure in a model may help to eliminate or confirm the application of the wafer as an important variable in the search for cause of leakage.

The method and the appliance may be used as an educational tool, to instruct users in how thorough they need to be in application of the wafer. Furthermore, it may be used to gain knowledge from users and where they apply pressure to the wafer and consider this information in further product development.

In a second aspect, the invention relates to an ostomy appliance comprising an adhesive wafer, the wafer comprising a backing layer facing away from the skin and an adhesive layer for attachment to the skin, the wafer comprising a sensing means capable of recording application of pressure to the wafer.

The sensing means may be integrated in the wafer. The sensing means may be in the form of a layer on the non-skin facing surface of the backing layer, or the backing layer or it may be embedded in the adhesive or it may be located between the backing layer and the adhesive.

The sensing means may have a size (area) corresponding to the wafer or smaller. Leakage usually develops from the central portion of the wafer, thus the sensing means may at least cover the central portion of the wafer.

The sensing means may be slightly larger, extending further radially than the wafer, in order to secure the edge portion is fully attached.

The sensing means may be in the form of a separate sheet overlying at least a part of the wafer. When the sensing means are in the form of a sheet on the non-skin facing surface of the backing film, the sheet may be detachable or permanently fixed to the backing layer. The sensing means may be in the form of a separate sheet being attached to a collection bag or the sensing mean may be incorporated in the bag material, or they may be provided inside the bag, in an area overlying at least a part of the wafer. The sheet may be permanently fixed to the bag or it may be detachable. A detachable sheet can be detached and entered into a medical journal or scanned for logging the data. The sensing means may be a part of the bag. The sensing means may be provided with a cover layer overlying at least a part of the non-skin facing surface of the sensing means. Such cover layer may hide the visual reaction on the sensing means until the cover layer is removed.

The pressure sensing means may be a pressure sensitive material developing a color change when exposed to pressure. The color change may occur immediately or within a few minutes after exposure to pressure of a predetermined force. The color reaction may be visible to the user or nurse.

There are several ways of achieving a color reaction as a result of a pressure impact. The pressure sensing material may be in the form of a two polymer sheet material provided with a coating on one or both the sheets. The coating may comprise chemical components that, when brought in direct contact with each other's will develop a color reaction. The coating may for example be in the form of small particles or microcapsules, where the particles or capsules may break and release their content, thereby producing a color reaction, when they are exposed to pressure. Or particles from the coating on one sheet is transferred to the other sheet, thereby producing a visible reaction.

The pressure sensing material may be in the form of a two polymer sheet material having small particles, that changes color, when they are pressed together. A two polymer sheet material that is used to illustrate pressure is placed on the wafer in order to show, where the user has touched the wafer. The two polymer sheets have small particles that changes color, when they are pressed together. Hence, when mounting the wafer the user will get instant visual feedback on whether the adhesive is sufficiently attached to the skin.

In one embodiment, the sensing means may be graphite paper.

The pressure sensing material may develop a change in optical properties/light transmission such that a visual change is observed when the material is exposed to pressure. The sensing means may comprise two layers of film overlying each other's, the first layer being transparent and provided with a rough coating, such as an adhesive layer, facing the second layer. When the layers are overlying each other's they may appear opaque or non-transparent due to the air trapped between the coating and the second layer and some light may be reflected by the coating. When the layers are pressed together, the air is squeezed out and the contact between the layers causes the light to be transmitted through the rough coating and hereby making the two layers appear more transparent/translucent. It is the same effect that appears when a strip of adhesive tape is loosely attached to a surface—the tape will be quite visible due to the air trapped in the rough surface of the adhesive and appear opaque, but when the tape is rubbed with a finger in order to firmly attach it to the surface, it may become more invisible (transparent/translucent) as the adhesive is forced into direct contact with the surface to which it is applied and the trapped air is squeezed out. Thus, the transmission or reflection of light of the sensing means is altered by application of pressure and the visual appearance of the tape is changed.

The coating or the backing layer may be provided with a tactile structure, such as a pattern coating in order to render the change more visible and/or tactile. The color change may encourage the user to touch and apply pressure the entire wafer. The direct feedback, may be an easy and informative way to let the user know, where the applied pressure and thereby the application of the wafer is (in)sufficient.

The sensing means may be used to reconstruct the application of pressure to the wafer afterwards. The color pattern obtained may be transformed into a three dimensional model or it may be logged in an electronic file.

The two-sheet material using small particles that when they collide and break upon contact/pressure will develop a color change, for example go from colorless to a bright red color. The intensity of the color may depend on the amount of pressure applied and the timeframe of which the pressure is applied. The wafer may be scanned or a photo is taken and the print may be converted into a 3D model and/or logged in the patient's file. The 3D model may give an indication of where the applied pressure was highest/lowest and it may be possible to reconstruct the same pressure using a silicone model.

The pressure sensing means may be a thermochromic material. Such material does not in itself directly respond to pressure, but records changes in temperature. However, the harder and/or longer the fingers are pressed or rubbed against the thermochromic material, the more the temperature will rise and the resulting color reaction will thus indirectly reflect the application of pressure.

Some thermochromic material may be reversible, thus the color will revert to the starting point over time. This opens up for the possibility that the sensing means can be reused. However, the thermochromic material may also be chosen to be non-reversible in order to save the recorded material. The fact that the sheet is responsive to heat, may also have the effect the user is encouraged to heat the wafer even more, which will result in a better adhesion of the wafer.

A heat sensitive sheet changes color due to temperature changes. Such thermochromic sheet may for example be a sheet comprising liquid crystals that change shape when heated and thereby reflect different wavelengths of light—which makes it change color.

Thermochromic polymers may be cast into the wafer or the backing layer of the wafer or the thermochromic polymers may be comprised in a separate sheet overlying at least a part of the wafer. The sheet may be unreleasably attached to the backing layer or it may be releasably attached for example by a weak adhesive.

The pressure sensitive material may be changing color when a predetermined threshold is exceeded. The sensitivity of the pressure sensing means may be adjusted to avoid pressure registration during handling of the wafer before application but only react when the pressure is high enough to have an impact on the adhesion to the skin.

The sensing means may be a pressure sensitive material developing a tactile change when exposed to pressure. This may be advantageous in the case where it is difficult for the user to observe the wafer during application, for example using a one-piece device or in the case of obesity.

The tactile change may be in the form of material that can be flattened, collapsed or displaced. The collapsible area may be the entire wafer surface or it may be a part thereof, for example the central part or in the form of dots or ridges that can be flattened when exposed to pressure.

The pressure sensing means may be in the form of a moldable mass, for example a moldable adhesive. The moldable mass may be provided in a topographical pattern that diminishes or disappear when exposed to pressure. In this way, a tactile response is achieved.

The sensing means may comprise a collapsible foam. The foam may be adapted to collapse when exposed to a predetermined pressure threshold. The threshold may be chosen to be a pressure that is sufficient to attach the adhesive properly and high enough to avoid pressure during the handling of the wafer before application to have impact on the result.

In one embodiment the material may be in the form of multiple gas-filled pockets, like bubble wrap. The pockets may be broken or collapsed when exposed to pressure. The breaking of the pockets may also produce a sound that may help the user to ensure that the applied pressure was high enough. Data may be logged by 3D scanning or by saving the sensing means for the journal.

The sensing means may be a pressure sensitive material developing an electronic impulse when exposed to pressure. The sensing means may be in the form of a separate sheet being attached to a collection bag, in an area overlying at least a part of the wafer. Such sheet may be reusable. In another embodiment, the sensing means are incorporated in the wafer.

Force-sensitive resistors (FSR) are able to record not only where the user applies pressure to the wafer, but also the degree of pressure being applied. Such sensor may be in the form of two layers separated by a conductive sheet. When the layers are pressed closer together the resistance of the sheet decreases, the change in resistance is measured and the signal converted into a data file in the computer. The sensor may define a pattern such as an x- and a y-axis or a bulls-eye pattern facilitating tracking a relatively precise position of the users touch, even with several touches are carried out simultaneously.

An interactive processor that makes it possible to convert any conductive object or surface to a keyboard input may also be used for electronic logging of applied pressure. As the FSR, the data can be logged and stored, and eventually reproduced.

The ostomy appliance may comprise an adhesive wafer. Such wafer may typically comprise a backing layer coated with an adhesive layer. The wafer may comprise an aperture for receiving a stoma or body opening. A collection bag may be connected to the wafer.

The bag may be detachable from the wafer or it may be integrated with the wafer. Such appliances may be two-piece or one-piece appliances. In both types of appliances, an adhesive wafer is attached to the wearer's skin. In case of a one-piece appliance, a receiving member or bag is attached to the adhesive wafer. In case of a two-piece appliance, the adhesive wafer forms part of a body side member and a receiving bag is attached releasably to the body side ostomy member for receiving exudates from the stoma.

The coupling means for use in connection with the present invention may be any suitable coupling means known per se for coupling of ostomy base plates to ostomy collecting bags, e.g. a mechanical coupling such as matching coupling rings such as the coupling rings disclosed in WO 91/01118 and WO 91/01119 or WO 94/18919 or matching flanges for adhesive connection of the type disclosed in U.S. Pat. No. 5,800,415.

In one embodiment the bag is provided with an outlet. The outlet facilitates the bag to be emptied and reused.

The appliance may be provided with more than one type of pressure sensing means, opening up for the possibility of combining two or more of the color changing, tactile or electronic registration means in any suitable manner and this is also a part of the invention.

The invention claimed is:

1. A method of monitoring pressure applied to an ostomy appliance by a person applying the ostomy appliance to skin, the ostomy appliance comprising an adhesive wafer comprising a backing layer facing away from the skin and an adhesive layer attached to the backing layer and adapted for attachment of the ostomy appliance to the skin, the method comprising:
    a) providing sensing means capable of recording an application of a pressure to the adhesive wafer,
    b) monitoring a location on the adhesive wafer where the person touched the adhesive wafer when applying the pressure and attaching the adhesive wafer to the skin surrounding a stoma,
    c) generating recorded data with the sensing means indicating the location on the adhesive wafer where the person touched the adhesive wafer when applying the adhesive wafer to the skin, and
    d) retrieving the recorded data from the sensing means.

2. The method according to claim 1, wherein the providing sensing means includes providing a pressure sensitive material adapted for developing a color change when exposed to pressure.

3. The method according to claim 1claim 2, wherein the providing sensing means includes providing a the pressure sensing material includes providing having two polymer sheets including a coating applied to at least one of the two polymer sheets, where the coating is adapted to change color when the two polymer sheets are pressed together.

4. The method according to claim 1, further comprising processing the recorded data into an electronic form.

5. The method according to claim 1, comprising integrating the sensing means into the adhesive wafer.

6. The method according to claim 1, comprising integrating the sensing means into the backing layer of the ostomy appliance.

7. The method according to claim 1, comprising embedding the sensing means into the adhesive layer of the ostomy appliance.

8. The method according to claim 1, comprising locating the sensing means between the adhesive layer and the backing layer of the ostomy appliance.

9. The method according to claim 1, comprising providing a detachable sensing means detachable from the backing layer of the ostomy appliance.

10. The method according to claim 1, further comprising providing feedback to a user indicating whether the user has applied a pressure that is sufficient for leak-free adherence of the adhesive wafer to the skin.

11. The method according to claim 1, further comprising measuring where a user has applied pressure to the adhesive wafer.

12. The method according to claim 1, further comprising monitoring and logging where a user has applied pressure to the adhesive wafer.

13. The method according to claim 3, wherein the coating comprises chemical components that change color when the chemical components contact each other.

14. The method according to claim 3, wherein the coating comprises microcapsules that are adapted to break and release contents of the microcapsules, the releasing of the contents of the microcapsules resulting in the change in the color.

15. The method according to claim 1, comprising retrieving the recorded data from the sensing means and converting the recorded data to a three-dimensional model indicating pressure application to the adhesive wafer.

16. The method according to claim 1, further comprising adjusting sensitivity of the sensing means to avoid pressure registration applied to the adhesive wafer during handling of the adhesive wafer and prior to applying the adhesive wafer to the skin.

17. A method of monitoring a user's pattern of movements when applying an ostomy appliance to skin, the ostomy appliance comprising an adhesive wafer comprising a backing layer facing away from the skin and an adhesive layer attached to the backing layer and adapted for attachment to the skin, the method comprising:
- integrating pressure sensing means into the adhesive wafer, where the pressure sensing means changes color in response to a pressure applied to the adhesive wafer when applying the adhesive wafer to the skin surrounding a stoma;
- monitoring a location on the adhesive wafer where a person touched the adhesive wafer and recording the pressure applied to the adhesive wafer with the pressure sensing means;
- retrieving recorded data from the sensing means; and
- providing feedback to the user informing the user of a level of pressure applied to the adhesive wafer.

18. A method of monitoring a person's application of an ostomy appliance to skin, the method comprising:

a) providing means for sensing a pressure applied to the ostomy appliance when applying the ostomy appliance to the skin;
b) monitoring a location where the person touched the ostomy appliance when applying the ostomy appliance to the skin around a stoma;
c) generating recorded data indicating the location where the person touched the ostomy appliance when applying the ostomy appliance to the skin; and
d) retrieving and saving the recorded data.

19. A method of monitoring a person's application of an ostomy appliance to skin, the method comprising:
a) providing the ostomy appliance with a pressure sensitive material adapted for developing a color change when exposed to a pressure applied to the ostomy appliance during application of the ostomy appliance to the skin;
b) monitoring, with the pressure sensitive material, a location where the person touched the ostomy appliance during the application of the ostomy appliance to the skin;
c) generating recorded data from the pressure sensitive material indicating the location where the person touched the ostomy appliance during the application of the ostomy appliance to the skin; and
d) retrieving and saving the recorded data.

20. A method of monitoring application of an ostomy appliance to skin, the ostomy appliance comprising an adhesive wafer comprising a backing layer facing away from the skin and an adhesive layer attached to the backing layer and adapted for attachment to the skin, the method comprising:
a) providing a sensor integrated with the adhesive wafer and capable of recording an application of pressure applied by a user to the adhesive wafer;
b) pressing the adhesive wafer against the skin surrounding a stoma;
c) measuring or monitoring the pressure applied by the user to the adhesive wafer; and
d) providing feedback to the user informing the user as to whether a sufficient pressure has been applied to the adhesive wafer.

21. A method of monitoring application of an ostomy appliance to skin, the method comprising:
- providing a sensor capable of recording application of pressure to the ostomy appliance;
- integrating the sensor into an ostomy adhesive wafer of the ostomy appliance, where the sensor changes color in response to pressure applied to the ostomy adhesive wafer during application of the ostomy appliance to the skin; and
- providing feedback to the user informing the user of a level of pressure applied to the adhesive wafer.

* * * * *

UNITED STATES PATENT AND TRADEMARK OFFICE
CERTIFICATE OF CORRECTION

| | |
|---|---|
| PATENT NO. | : 10,736,769 B2 |
| APPLICATION NO. | : 14/905812 |
| DATED | : August 11, 2020 |
| INVENTOR(S) | : Grove Sund et al. |

Page 1 of 1

It is certified that error appears in the above-identified patent and that said Letters Patent is hereby corrected as shown below:

In the Specification

In Column 1, Line 66, delete "solved" and insert -- to be solved --, therefor.

In the Claims

In Column 6, Line 52, in Claim 3, delete "claim 1claim 2," and insert -- claim 2, --, therefor.

In Column 6, Line 53, in Claim 3, delete "a the" and insert -- the --, therefor.

Signed and Sealed this
Second Day of March, 2021

Drew Hirshfeld
*Performing the Functions and Duties of the
Under Secretary of Commerce for Intellectual Property and
Director of the United States Patent and Trademark Office*